United States Patent [19]

Chernousov et al.

[11] Patent Number: 4,485,811
[45] Date of Patent: Dec. 4, 1984

[54] RESECTION APPARATUS

[75] Inventors: Alexandr F. Chernousov; Sergei A. Domrachev, both of Moscow; Alexei I. Ivanov, Kalinin; Boris N. Malyshev, Moscow; Viktor A. Saljuk, Moscow; Oleg K. Skobelkin, Moscow; Evgeny I. Brekhov, Moscow, all of U.S.S.R.

[73] Assignee: Vsesojuzny Nauchny Tsentr Khirurgii, Moscow, U.S.S.R.

[21] Appl. No.: 372,140

[22] Filed: Apr. 27, 1982

[30] Foreign Application Priority Data

Feb. 8, 1980 [SU] U.S.S.R. ............................. 2881888

[51] Int. Cl.³ .................................................. A61B 17/36
[52] U.S. Cl. .............................. 128/303.1; 128/334 R
[58] Field of Search ............ 128/303.1, 395–398, 128/334 R, 335 R

[56] References Cited

U.S. PATENT DOCUMENTS 4,143,660 3/1979 Malyshev et al. ............ 128/303.1

FOREIGN PATENT DOCUMENTS 1276239 6/1972 United Kingdom ............ 128/334 R
189517 6/1960 U.S.S.R. ............................. 128/335
209629 4/1968 U.S.S.R. .
511939 6/1976 U.S.S.R. .
625696 8/1978 U.S.S.R. ............................. 128/303.1
584439 7/1979 U.S.S.R. ............................. 128/303.1

Primary Examiner—Lee S. Cohen
Attorney, Agent, or Firm—Fleit, Jacobson, Cohn & Price

[57] ABSTRACT

The resection apparatus includes a cutting instrument, e.g., a laser beam, and a unit for suturing the organ being resected, incorporating an oblong die with depressions for staples to bend, an oblong detachable staple body with a staple magazine and a staple ejector. A holder of the staple body has two members and, of which the first member is arranged parallel to the die and is rigidly coupled thereto, whereas the second member is arranged square with the former one, is offset transversely with respect to it and carries a retainer, to lock the staple body in position. Provision is also made in the apparatus for a hold-down frame set on the second member transversely in the plane of movement of the staple body so as encompass, while in one of its positions, the die along the external perimeter thereof for clamping the organ being resected. The first member has guideways for the cutting instrument to set and traverse.

4 Claims, 4 Drawing Figures

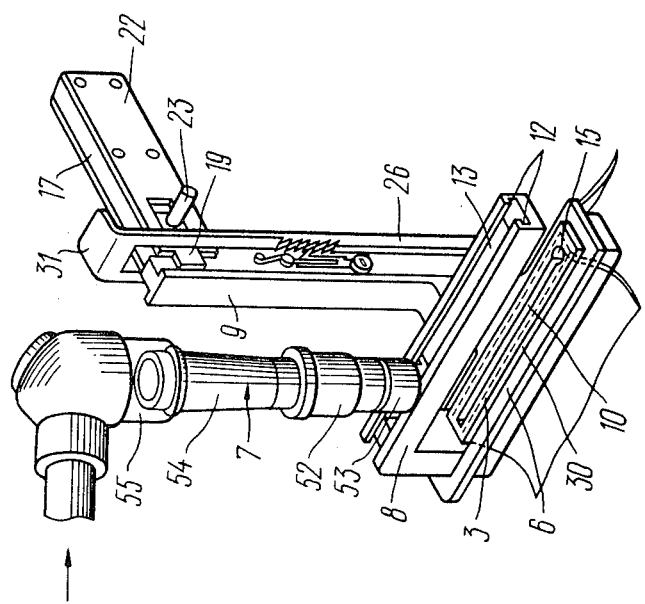
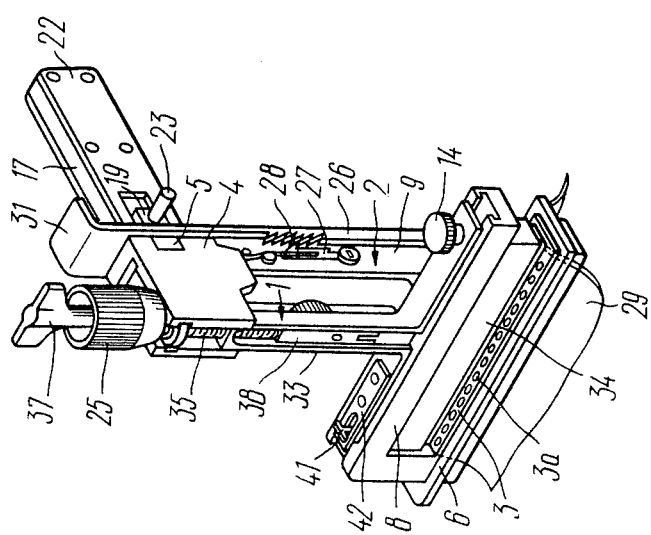

RESECTION APPARATUS

FIELD OF THE INVENTION

The present invention relates generally to medicine, more specifically to surgery and has particular reference to an apparatus for resction of human organs, especially those seated in hard to access places.

BACKGROUND OF THE INVENTION

Known in the present state of the medical art are instruments for suturing human organs with metallic staples, wherein the part of the organ being resected is cut off mechanically, i.e., by a knife after suturing (cf., e.g., USSR Inventor's Certificate No. 511,939). However, when applying such suturing instruments it is extremely difficult to use an electrotome or plasma scalpel or a laser beam as the cutting instruments. On the other hand, it is common knowledge that mechanical dissection fails to provide an aseptic and bloodless incision.

Another apparatus for staple suturing and dissecting by virtue of a laser beam as disclosed in U.S. Pat. No. 4,143,660, is known to comprise a staple body and a supporting body, each being separately applied to the organ operated upon and joined together by a special locking device, a cutting instrument, an optical waveguide for a laser beam or a mechanical knife traversable along the staple body. However, such an apparatus cannot successfully be applied for resections in hard to access places (such as the cardiac portion of the stomach, the small pelvis, thoracic cavity). In addition, resection of human organs with the use of the apparatus according to said patent requires extensive mobilization of the organ operated upon which involves considerable traumatization of the surrounding tissues, increased loss of blood and complicated operative techniques.

Another apparatus for suturing the gastric walls with pi-shaped staples and resection as described in USSR Inventor's Certificate No. 209,629, comprises a cutting instrument and a suturing unit for the organ being resected which incorporates an oblong die provided with depressions for staples to bend, a staple body with a magazine and a staple ejector, said staple being mounted on its holder comprising a member arranged parallel to the die and rigidly held thereto, and another member arranged square with the first one in the plane of movement of the staple body.

However, the construction features of said apparatus fail to provide an aseptic incision of the tissue operated upon, since the member arranged parallel to the die and the other member arranged square with the former one are interconnected square with each other so that the former member along with the staple body lie in the same plane, that is, in the plane of movement of the staple body, which prevents the application of a change cutting instrument, in particular a laser beam, whereby an aseptic incision cannot be produced.

SUMMARY OF THE INVENTION

It is an object of the present invention to provide such a resection apparatus that would ensure aseptic operative procedure in hard to access places involving minimized amount of traumatized tissues and loss of blood.

It is another object of the present invention to provide such a resection apparatus that would ensure a reliable fixing of the organ being resected both in the course of suturing and resecting in hard to access places with a possibility of merely replacing one cutting instrument by another.

It is one more object of the pesent invention to provide such a resection apparatus that would ensure a possibility of applying a variety of cutting instruments in the same apparatus.

It is still one more object of the present invention to provide a possibility of using a laser-beam cutting instrument in the resection apparatus involved, so as to ensure full aseptic conditions.

It is yet still one more object of the present invention to provide a possibility of visual monitoring of the cutting process with the use of a laser-beam cutting instrument.

And it is an additional object of the present invention to provide a resection apparatus of the character set forth hereinbefore that would ensure a lower extent of injury to the surrounding tissues.

Said and other objects are accomplished due to the fact that in a resection apparatus, comprising a cutting instrument and a suturing unit which incorporates an oblong die with a number of depressions for staples to bend, an oblong staple body with a staple magazine and a staple ejector, said staple body being detachably mounted on its holder and having a first member arranged parallel to the die and rigidly coupled thereto, and a second member arranged square with said first member in the plane of movement of the staple body and rigidly fixed to said first member, according to the present invention, the second member of the holder is offset transversely with respect to the first member so as to lie off the plane of movement of the staple body, and carries a retainer to lock the staple body in position, and provision is also made for a hold-down frame mounted on the second member traversably in the plane of movement of the staple body so as to encompass, while in one of its positions, the die along the external perimeter thereof, whereas guideways are provided on the first member for the cutting instrument to move.

An advantageous feature of the herein-proposed resection apparatus resides in that the transversely offset position of the second member of the holder with respect to the first member thereof makes it possible, after suturing the organ operated upon, to remove the staple body and replace it by any cutting instrument, in particular an optical waveguide of laser emission, in order to provide an aseptic resection in a hard to access zone of surgical intervention, while the retainer ensures high rate of such a replacement. The hold-down frame enables the tissue to be reliably fixed to the die after suturing which ensures against any dislodging of the sutured organ after removal of the staple body. Thus, a pinpoint accuracy of cutting is attained which is of special importance when a laser-beam cutting instrument is resorted to. In addition, the guideways provided in this resection apparatus rule out any deviation of the cutting instrument.

One of the embodiments of the present invention provides for the use of a laser-beam cutting instrument known 'per se' whose optical waveguide is accommodated in a head mounted in guideways, a gap being provided between the guideways for the laser beam to pass.

BRIEF DESCRIPTION OF THE DRAWINGS

In what follows the present invention is illustrated by a description of a specific but not restricting embodiment thereof to be read with reference to the accompanying drawings, wherein:

FIG. 1 is a perspective view of a resection apparatus, according to the present invention, when assembled and put in working position of the organ being resected;

FIG. 2 is a perspective view of a resection apparatus, according to the present invention, with the staple body removed and the optical waveguide of laser emission installed in the guideways of the first member of the staple body holder;

DETAILED DESCRIPTION OF THE INVENTION

Figure 4:
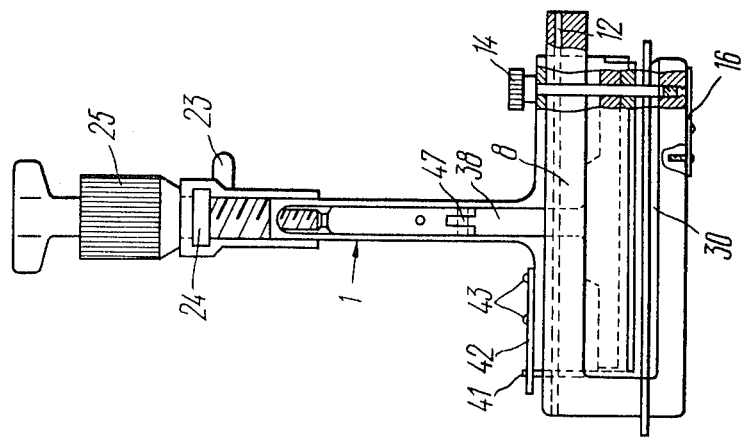
FIG. 4 is a front fragmentarily cutaway view of a resection apparatus, according to the present invention.

Referring now to the accompanying drawings the resection apparatus comprises the following units and components: a staple body 1, a holder 2 of the staple body 1, a die 3 with depressions 3a, a bracket 4 with a slot 5, a hold-down frame 6, an optical waveguide 7 of laser emission (not shown), whose beam serves as a cutting instrument. The laser is not shown for the sake of easy reading of the drawings. Moreover the laser itself is irrelevant to the essence of the present invention and there may be used as such a laser any one of the currently used lasers capable of providing adequate emissive power, e.g., the "Scharplan" laser device.

The holder 2 comprises a first member 8 arranged parallel to the die 3 and coupled rigidly thereto, and a second member 9 rigidly interconnected with the first member 8 of the holder 2. The first member 8 and the die 3 are made integral with each other so that such an integral piece is yoke-shaped. The die 3 carries a number of the depressions 3a for bending the staples fed from the staple body 1, and has a slot 10 (FIG. 2) for the cutting instrument to pass, as well as another slot 11 to accommodate a supporting plastics insert (not shown for the sake of easy reading of the drawing) whose shape follows that of the slot 11 and involved in cutting the tissue with the knife. The first member 8 of the holder 2 has guideways 12 for the optical waveguide 7 to traverse, as well as an opening 13 for centre-aligning and guiding the staple body 1. To provide more rigidity during the suturing the first member 8 and the die 3 are associated by a screw 14 (FIG. 1) which passes through a hole 15 (FIG. 2) in the die 3 situated between the rows of depressions. The hole 15 is closed by a plate 16 (FIGS. 3, 4) so as to prevent the laser beam from injuring the subjacent tissues and organs.

The second member 9 of the holder 2 has a T-shaped profile, is rigidly coupled to the first member 8 of the holder 2 and is offset with respect to the first member 8 along its transverse axis a length required in a given particular case for the laser waveguide 7 to set on the guideways 12 of the first member.

A handle 17 is provided in the top portion of the second member 9 of the holder 2, made integral with said member. A slot 18 is made in the handle 17 for a rod 19 to pass, said rod entering with its end the slot 5 of the bracket 4, whereby the staple body 1 is locked in place on the second member 9 of the holder 2.

The rod 19 is traversable along the slot 18 of the handle 17 under the action of a spring 20 which is centred about a stud 21. The slot 18 in the handle 17 accommodating the rod 19 and the spring 20 is closed on both sides by side members 22. A handhold 23 is for the rod 19 to retract into the slot 18 of the handle 17.

The top portion of the second member 9 of the holder 2 carries the bracket 4 to fix the staple body 1 in position. The bracket 4 has a slot 24 to accommodate a nut 25. The centre of the slot 24 coincides with the centre of the opening 13 in the first member 8 and with that of the slot 10 in the die 3, whereby the staple body 1 can be centre-aligned with respect to the opening 13 in the first member 8 and the die 3.

The second member 9 carries a link 26 of the hold-down frame 6 which is traversable in the plane of movement of the staple body 1 independently of the latter by means of the link 26. While in one of its positions (when fixing the organ being resected) the hold-down frame 6 is locked by a latch 27 actuated by a spring 28. When in this extreme position the hold-down 6 encompasses the die 3 along the external perimeter thereof so that the edge of the hold-down frame interacts with the tissue of an organ 29 to fix it on bevelled edges 30 of the die 3, at the same time stretching the tissue and forcing it against the die. A flange 31 is provided at the top of the link 26 of the hold-down frame 6 for conveniently moving the latter. A screw 32 is envisaged for the hold-down frame to lock in the topmost position.

The staple body 1 has a tailpiece 33 and a staple head 34. The top portion of the tailpiece 33 of the staple body 1 has a male thread 35 which engages the nut 25 for the staple body 1 to travel with respect to the bracket 4, as well as a female thread 36 to engage a screw 37 for a staple ejector 38 to actuate.

The staple head 34 has a T-slot 39 adapted to accommodate a change staple magazine 40 which is locked on the staple body 1 by a slider 41 actuated by a flat spring 42 made fast on the staple body 1 by screws 43. The staple head 34 of the staple body 1 enters the opening 13 in the first member 8 of the holder 2 and, while traversing, with its lugs 44 rests against the top surface of the first member 8, whereby a constant clearance between the magazine 40 and the die 3 is defined.

The ejector 38 has a slot 45 to accommodate a pressure head 46 of the screw 37, and is provided in its middle portion with a hinge joint 47 necessary for disassembling and removing the ejector 38 from the staple body 1. A screw 48 passing through a slot 49 in the staple body 1 prevents the hinge joint 47 against spontaneous disengaging from the screw 37. The ejector 38 carries two rows of ejecting plates 50 to drive pi-shaped staples out of the magazine 40.

A change knife 51 is interposed between the ejecting plates 50. Changeability of the knife makes it possible to carry out an operation by any technique without replacing the ejector 38, e.g., using the knife for dissecting the tissues, or without a knife, by applying any other cutting instrument, a laser beam in this particular case.

The laser waveguide 7 comprises a head 52 with a T-shaped endpiece 53 made of polytetrafluoroethylene and adapted to engage the guideways 12 of the first member 8 of the holder 2, said member being arranged parallel to the die 3.

A tube 54 is held to the head 52 by a thread (not shown), said tube being in turn held to a focussing objective 55 of the laser device through a thread (not shown).

Figure 3:
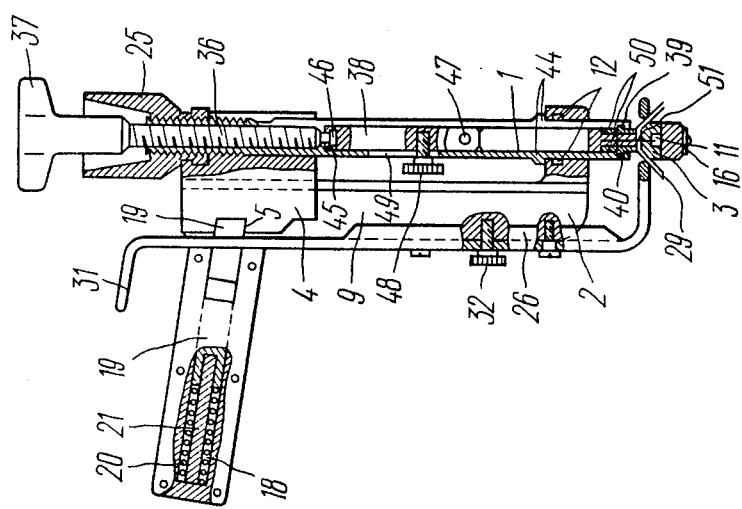
FIG. 3 is a side fragmentarily cutaway view of a resection apparatus, according to the present invention.

Now let us consider a surgical intervention with the use of the laser beam as a cutting instrument. In this case the knife 51 must be removed from the ejector 38. The apparatus assembled as shown in FIGS. 1 and 3 and a required number of the change magazines loaded with staples, are subject to sterilization by any conventional method, e.g., in an autoclave. The optical waveguide is sterilized separately in 96-percent ethanol. The operative procedure is performed as follows.

The staple body 1 with the bracket 4 is fitted onto the holder 2 and the bracket 4 is locked by the rod 19. The hold-down frame 6 is fixed in its topmost position. The apparatus is brought behind the organ to be resected, whereupon the hold-down frame 6 is let to move down by pressing the flange 31, and the organ 29 is fixed to the die 3. Then the staple body is actuated by the nut 25 to move down till meeting the top surface of the member 8, and the latter is connected to the die 3 by the screw 14.

While so doing one must observe that the ejector 38 should be in the topmost position, whereupon the screw 37 is rotated to move the ejector 38 all the way down to varying suturing with staples arranged in two parallel rows.

The suturing over the screw 14 is turned out, the retainer 19 is forced out and the bracket 4 along with the staple body a is removed from the holder 2. Then the optical waveguide 7 connected to the laser device (not shown) is put on the guideways 12 of the member 8. Once the laser has been fired the focussed laser beam is directed by the waveguide to pass in-between the rows of staples and get onto the organ being resected. Thus, traversing the waveguide 7 along the guideways 12 of the member 8 one can perform an aseptic and bloodless resection of the organ operated upon. This done the laser is turned out, the hold-down frame 6 is moved all the way up and locked by the screw 32, and the apparatus is removed from the resected organ. This terminates the operative procedure.

When mechanical resection of the tissue is resorted to the knife 51 is not removed from the ejector 38, and a plastics insert (not shown) is fitted into the slot 11 of the die 3. With the ejector 38 moved by the screw 37 the organ operated upon is resected by the knife 51 and staple-sutured at the same time.

Thus, the proposed resection apparatus enables one to perform an aseptic and a traumatic resection of human organs seated in hard to access places with the minimized extent of injury to the surrounding tissues and practically without bleeding. The application of the apparatus simplifies the operative techniques, renders any complications due to infecting the operative field less probable, cuts down the operating time, facilitates the surgeon's labour and provides better conditions for the surgical intervention as a whole.

It must be noted that the apparatus is applicable not only for resection of human organs but also for formation of transplants from the stomach to establish a pediculate gastroma.

Although the present invention has been described with reference to a preferred embodiment thereof and to a specific drawing, it should be understood to those skilled in the art that various changes and modifications may be made within the scope of the claims that follow. Thus, there may be provided the provision of staple depressions arranged square with the above-described rows on one of the end faces so as to obtain a pi-shaped suture, which is especially expedient for formation of transplants from the stomach when the apparatus is applied to the stomach several times in succession, for instance, in the case of transplant formation according to Gavrilin, or for formation of an isoperistaltic tube from the greater curvature of the stomach.

What we claim is:

1. A resection apparatus comprising a die for bending staples, a holder having a first member parallel to said die and rigidly coupled thereto and a second member offset transversely of said first member and rigidly connected to said first member, said first member including means for receiving, interchangeably, a stapling device or a cutting device so as to position the stapling device or the cutting device in an operational relationship with the die, said second member including retainer means for locking said stapling device in position when received in said means for receiving and a hold-down frame mounted on said second member transversebly in the plane of movement of said stapling device, said first member provided with guide ways, said guide ways adapted for said cutting device to move on.

2. An apparatus according to claim 1 and further comprising a staple body, including a magazine containing staples and an ejector received in said means for receiving.

3. An apparatus according to claim 1 and further comprising a cutting device received in said means for receiving.

4. The apparatus of claim 3 wherein the cutting device is a laser guide.

* * * * *